(12) United States Patent
Kleindienst et al.

(10) Patent No.: US 10,806,381 B2
(45) Date of Patent: Oct. 20, 2020

(54) AUDIOLOGY TESTING TECHNIQUES

(71) Applicant: Mayo Foundation for Medical Education and Research, Rochester, MN (US)

(72) Inventors: Samantha J. Kleindienst, Mesa, AZ (US); David A. Zapala, Ponte Vedra Beach, FL (US); Greta C. Stamper, Ponte Vedra Beach, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 136 days.

(21) Appl. No.: 16/081,237

(22) PCT Filed: Feb. 27, 2017

(86) PCT No.: PCT/US2017/019626
§ 371 (c)(1),
(2) Date: Aug. 30, 2018

(87) PCT Pub. No.: WO2017/151482
PCT Pub. Date: Sep. 8, 2017

(65) Prior Publication Data
US 2019/0069811 A1 Mar. 7, 2019

Related U.S. Application Data

(60) Provisional application No. 62/301,750, filed on Mar. 1, 2016.

(51) Int. Cl.
*A61B 5/12* (2006.01)
*A61B 5/00* (2006.01)

(52) U.S. Cl.
CPC .............. *A61B 5/126* (2013.01); *A61B 5/121* (2013.01); *A61B 5/4005* (2013.01); *A61B 5/4803* (2013.01)

(58) Field of Classification Search
USPC ...................................................... 704/1–504
See application file for complete search history.

(56) References Cited

U.S. PATENT DOCUMENTS 5,197,332 A * 3/1993 Shennib ................. A61B 5/121
600/559
5,792,072 A * 8/1998 Keefe ...................... A61B 5/12
600/559

(Continued)

OTHER PUBLICATIONS

BioBank [online], "Hearing 'Speech-in-Noise' Test", UK Biobank, Aug. 2012, retrieved on Apr. 10, 2017, URL<https://biobank.ctsu.ox.ac.uk/crystal/docs/Hearing.pdf>, 9 pages.

(Continued)

*Primary Examiner* — Marcus T Riley
(74) *Attorney, Agent, or Firm* — Fish & Richardson P.C.

(57) ABSTRACT

Speech understanding in the presence of background noise can be assessed using novel hearing tests. One such test is a Masking Level Difference with Digits (MLDD) test, which is a clinical tool designed to measure auditory factors that influence the understanding of speech presented within a background of noise. The MLDD test can be used clinically to facilitate a determination of functional hearing. The MLDD test presents background noise using both monotic and diotic conditions.

4 Claims, 3 Drawing Sheets

(56) References Cited

U.S. PATENT DOCUMENTS

| | | | | |
|---|---|---|---|---|
| 6,167,138 | A * | 12/2000 | Shennib | G16H 40/40 381/60 |
| 7,020,581 | B2 * | 3/2006 | Dittberner | H04R 25/30 702/183 |
| 7,288,071 | B2 * | 10/2007 | Harrison | A61B 5/12 600/559 |
| 7,340,062 | B2 * | 3/2008 | Revit | H04R 25/70 381/17 |
| 7,366,656 | B2 * | 4/2008 | Furst-Yust | G10L 15/02 704/200.1 |
| 7,398,204 | B2 | 7/2008 | Najaf-Zadeh | |
| 7,464,029 | B2 * | 12/2008 | Visser | G10L 21/0272 704/210 |
| 7,983,907 | B2 * | 7/2011 | Visser | G10L 21/0208 704/227 |
| 8,660,281 | B2 * | 2/2014 | Bouchard | H04R 25/43 381/312 |
| 8,892,232 | B2 * | 11/2014 | Suhami | G10L 21/0205 700/94 |
| 8,918,197 | B2 * | 12/2014 | Suhami | H04M 3/569 700/94 |
| 9,031,270 | B2 * | 5/2015 | Pontoppidan | H04R 25/353 381/316 |
| 9,031,271 | B2 * | 5/2015 | Pontoppidan | H04R 25/353 381/316 |
| 2001/0040969 | A1 * | 11/2001 | Revit | H04R 25/70 381/60 |
| 2004/0064066 | A1 * | 4/2004 | John | A61B 5/04845 600/559 |
| 2004/0158431 | A1 * | 8/2004 | Dittberner | H04R 25/30 702/183 |
| 2004/0204659 | A1 * | 10/2004 | John | A61B 5/04845 600/559 |
| 2005/0018858 | A1 * | 1/2005 | John | A61B 5/121 381/60 |
| 2005/0069162 | A1 * | 3/2005 | Haykin | H04R 25/552 381/312 |
| 2006/0153396 | A1 * | 7/2006 | John | A61B 5/121 381/60 |
| 2006/0253278 | A1 * | 11/2006 | Furst-Yust | G10L 15/02 704/209 |
| 2007/0021958 | A1 * | 1/2007 | Visser | G10L 21/0272 704/226 |
| 2007/0276270 | A1 * | 11/2007 | Tran | A61B 5/002 600/508 |
| 2007/0297626 | A1 * | 12/2007 | Revit | H04S 3/00 381/307 |
| 2008/0201138 | A1 * | 8/2008 | Visser | G10L 21/0208 704/227 |
| 2010/0002886 | A1 * | 1/2010 | Doclo | H04R 25/552 381/23.1 |
| 2010/0150387 | A1 * | 6/2010 | Dijkstra | H04R 25/554 381/315 |
| 2011/0087130 | A1 * | 4/2011 | Cheema | A61B 5/121 600/559 |
| 2011/0301486 | A1 * | 12/2011 | Van Hek | A61B 5/121 600/544 |
| 2011/0305345 | A1 * | 12/2011 | Bouchard | G10L 21/0208 381/23.1 |
| 2011/0313315 | A1 * | 12/2011 | Attias | G06F 19/00 600/559 |
| 2012/0197153 | A1 * | 8/2012 | Kraus | A61B 5/16 600/545 |
| 2013/0337796 | A1 * | 12/2013 | Suhami | H04R 25/00 455/422.1 |
| 2019/0069811 | A1 * | 3/2019 | Kleindienst | A61B 5/4803 |

OTHER PUBLICATIONS

Costalupes et al., "Effect of continuous noise backgrounds on reate response of auditory nerve fibers in cat," J Neurophysiology, Jun. 1984, 51(6): 1326-1344.

PCT International Search Report and Written Opinion in International Appln. No. PCT/US2017/019626, dated May 10, 2017, 10 pages.

PCT International Preliminary Report on Patentability in International Application PCT/US2017/019626, dated Sep. 4, 2018, 7 pages.

* cited by examiner

AUDIOLOGY TESTING TECHNIQUES

CROSS-REFERENCE TO RELATED APPLICATIONS

This application is a National Stage application under 35 U.S.C. § 371 of International Application No. PCT/US2017/019626, having an International Filing Date of Feb. 27, 2017, which claims priority to U.S. Application Ser. No. 62/301,750, filed on Mar. 1, 2016. This disclosure of the prior application is considered part of (and is incorporated by reference in) the disclosure of this application.

BACKGROUND

1. Technical Field

This document relates to methods for audiology and otology testing. For example, this document relates to methods for assessing speech understanding in the presence of background noise.

2. Background Information

In daily life, understanding speech spoken in background noise is a common occurrence that requires a certain level of hearing ability and listening strategy. The ability to understand speech in background noise can be impaired with various forms of hearing loss and it is important to measure any functional disability associated with hearing loss. There is tremendous variability in the potential settings in which speech must be understood within a context of background sound, and the perceptual and cognitive strategies that may be employed to accomplish understanding can vary from one setting to another and one person to another. However, it is clear that hearing loss, noise, and age, adversely affect understanding speech in the presence of noise.

Costalupes et al. (1984) found that at the level of auditory nerve fibers, low spontaneous rate fibers have higher thresholds and wider dynamic ranges, making them significantly more resistant to saturation by high noise levels. The authors determined that in the presence of background noise auditory nerve fibers change their dynamic range and response rate, concluding that these changes allow the nerve fibers to essentially function at roughly constant signal-to-noise ratios over a wide range of noise levels.

Further animal studies by Kujawa and colleagues (2006, 2009, 2013) have demonstrated primary degeneration of the cochlear nerve with exposure to noise, as well as effects of aging, particularly in the reduced population of low and medium spontaneous rate fibers. The authors hypothesize that the loss or dysfunction of these selective fibers contributes to the issue of hearing in noisy environments.

SUMMARY

This document provides methods for audiology and otology testing. For example, this document provides methods for assessing speech understanding in the presence of background noise.

Difficulty of hearing or understanding speech in background noise is a common complaint registered in audiology clinics. With rare exceptions, neural degeneration or damage in the central auditory nervous system via noise-exposure, age, or disease does not produce changes in pure tone or speech thresholds. Thus, diagnostic procedures that only involve these testing methods result in poor detection of functional hearing and central auditory disease and degeneration. As such, tools sensitive to speech understanding in background noise are important for the detection of neural dysfunction and decline.

In one implementation, a method of testing a participant's ability to accurately detect speech in the presence of background noise includes: (a) audibly presenting a first series of single-digit numbers to a first ear of the participant while a first background noise at a first signal-to-noise ratio (SNR) is audibly presented to the first ear but not to a second ear of the participant; (b) receiving, from the participant, a first group of results that reflect the participant's attempt at accurately reproducing the first series of single-digit numbers; (c) audibly presenting a second series of single-digit numbers to the first ear while a second background noise at a second SNR is audibly presented to the first ear and to the second ear; and (d) receiving, from the participant, a second group of results that reflect the participant's attempt at accurately reproducing the second series of single-digit numbers.

Such a method of testing a participant's ability to accurately detect speech in the presence of background noise may optionally also include: (e) audibly presenting a third series of single-digit numbers to the second while a third background noise at a third SNR is audibly presented to the second ear but not to the first ear; (f) receiving, from the participant, a third group of results that reflect the participant's attempt at accurately reproducing the third series of single-digit numbers; (g) audibly presenting a fourth series of single-digit numbers to the second ear while a fourth background noise at a fourth SNR is audibly presented to the second ear and to the first ear; and (h) receiving, from the participant, a fourth group of results that reflect the participant's attempt at accurately reproducing the fourth series of single-digit numbers.

In another implementation, a method of testing a participant's ability to accurately detect speech in the presence of background noise includes: (a) audibly presenting a first series of single-digit numbers to a first ear of the participant while a first background noise at a first signal-to-noise ratio (SNR) is audibly presented to the first ear but not to a second ear of the participant; (b) receiving, from the participant, a first group of results that reflect the participant's attempt at accurately reproducing the first series of single-digit numbers; (c) audibly presenting a second series of single-digit numbers to the first ear while a first type of second background noise at a second SNR is audibly presented to the first ear and while a second type of second background noise that differs from the first type of second background noise is audibly presented to the second ear; and (d) receiving, from the participant, a second group of results that reflect the participant's attempt at accurately reproducing the second series of single-digit numbers.

Such a method of testing a participant's ability to accurately detect speech in the presence of background noise may optionally also include: (e) audibly presenting a third series of single-digit numbers to the second while a third background noise at a third SNR is audibly presented to the second ear but not to the first ear; (f) receiving, from the participant, a third group of results that reflect the participant's attempt at accurately reproducing the third series of single-digit numbers; (g) audibly presenting a fourth series of single-digit numbers to the first ear while a first type of fourth background noise at a fourth SNR is audibly presented to the first ear and while a second type of fourth background noise that differs from the first type of fourth background noise is audibly presented to the second ear; and (h) receiving, from the participant, a fourth group of results that reflect the participant's attempt at accurately reproducing the fourth series of single-digit numbers.

In another implementation, a hearing test system for testing a participant's ability to accurately detect speech in the presence of background noise is configured to: (a) audibly present a first series of single-digit numbers to a first ear of the participant while a first background noise at a first signal-to-noise ratio (SNR) is audibly presented to the first ear but not to a second ear of the participant; (b) receive, from the participant, a first group of results that reflect the participant's attempt at accurately reproducing the first series of single-digit numbers; (c) audibly present a second series of single-digit numbers to the first ear while a second background noise at a second SNR is audibly presented to the first ear and to the second ear; and (d) receive, from the participant, a second group of results that reflect the participant's attempt at accurately reproducing the second series of single-digit numbers.

Such a hearing test system for testing a participant's ability to accurately detect speech in the presence of background noise may optionally be configured to: (e) audibly present a third series of single-digit numbers to the second while a third background noise at a third SNR is audibly presented to the second ear but not to the first ear; (f) receive, from the participant, a third group of results that reflect the participant's attempt at accurately reproducing the third series of single-digit numbers; (g) audibly present a fourth series of single-digit numbers to the second ear while a fourth background noise at a fourth SNR is audibly presented to the second ear and to the first ear; and (h) receive, from the participant, a fourth group of results that reflect the participant's attempt at accurately reproducing the fourth series of single-digit numbers. In some embodiments, the hearing test system comprises a personal computer.

In another implementation, a hearing test system for testing a participant's ability to accurately detect speech in the presence of background noise is configured to: (a) audibly present a first series of single-digit numbers to a first ear of the participant while a first background noise at a first signal-to-noise ratio (SNR) is audibly presented to the first ear but not to a second ear of the participant; (b) receive, from the participant, a first group of results that reflect the participant's attempt at accurately reproducing the first series of single-digit numbers; (c) audibly present a second series of single-digit numbers to the first ear while a first type of second background noise at a second SNR is audibly presented to the first ear and while a second type of second background noise that differs from the first type of second background noise is audibly presented to the second ear; and (d) receive, from the participant, a second group of results that reflect the participant's attempt at accurately reproducing the second series of single-digit numbers.

Such a hearing test system may optionally also be configured to: (e) audibly present a third series of single-digit numbers to the second while a third background noise at a third SNR is audibly presented to the second ear but not to the first ear; (f) receive, from the participant, a third group of results that reflect the participant's attempt at accurately reproducing the third series of single-digit numbers; (g) audibly present a fourth series of single-digit numbers to the first ear while a first type of fourth background noise at a fourth SNR is audibly presented to the first ear and while a second type of fourth background noise that differs from the first type of fourth background noise is audibly presented to the second ear; and (h) receive, from the participant, a fourth group of results that reflect the participant's attempt at accurately reproducing the fourth series of single-digit numbers. In some embodiments, the system can include a personal computer.

Particular embodiments of the subject matter described in this document can be implemented to realize one or more of the following advantages. In some embodiments, the hearing tests provided herein combine a digits-in-noise paradigm and a release from masking paradigm to assess primitive speech (digit) recognition in spatialized noise. Such a method can isolate hearing function from other aspects, such as linguistic ability, to provide a more accurate hearing assessment. In some embodiments, the tests provided herein advantageously assesses the release from masking effect by modifying the spectral and temporal structure of masking noise independent of the overall perception of loudness. In some embodiments, malingering performance on the hearing tests can be detected, making the tool useful for quantification of the functional (ICF) aspect of the deficit in speech in noise recognition. In some embodiments, the test performance can be used to indicate the presence of disease affecting the auditory system.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

Figure 1:
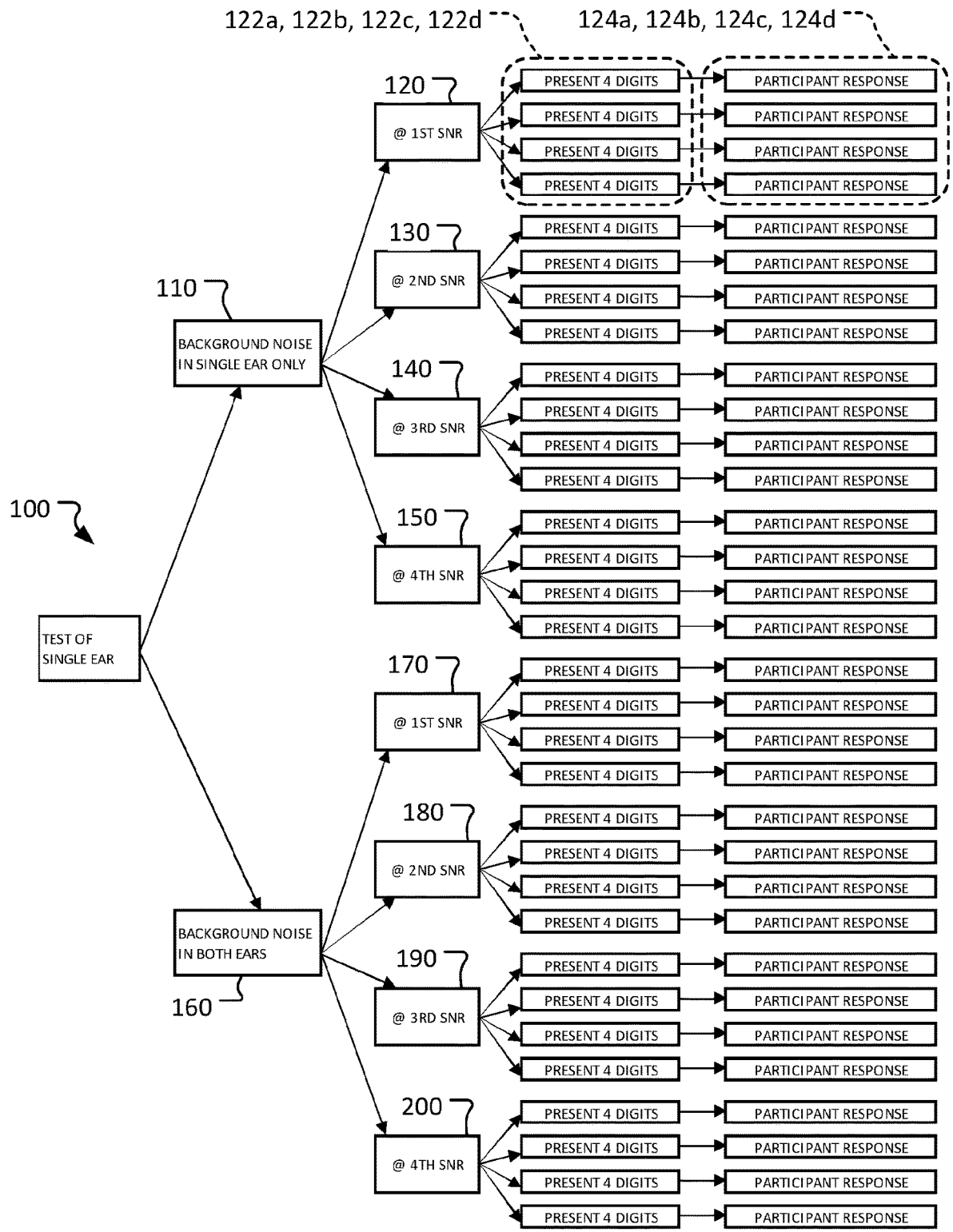
FIG. 1 is a flowchart depicting an example method for performing a hearing test in accordance with some embodiments provided herein.

This document provides methods for audiology and otology testing. In particular, this document provides methods for assessing speech understanding in the presence of background noise. For example, one such method is referred to herein as the Masking Level Difference with Digits (MLDD) test. The MLDD test is a clinical tool designed to measure auditory factors that influence the understanding of speech presented within a background of noise. The MLDD test can be used clinically to facilitate a determination of functional hearing. The MLDD test is unique in how it presents background noise using both monotic and diotic conditions.

The impetuses behind the development of the MLDD test include a need for: a simple speech in noise task that is linguistically primitive (does not require high level linguistic processing), sensitivity to the function of the auditory nerve (e.g. the low spontaneous rate fibers), and controls for volitional misreporting of clearly recognized items on the test (resistance to malingering).

The MLDD test measures the masking level difference (MLD) and the binaural release from masking effect, which happens at the level of the auditory nerve and the lower brainstem. The MLD is the psychoacoustic phenomenon involving the change in threshold between two test conditions (e.g., interaural phase differences of signal or noise, or monotic versus diotic conditions). The binaural release from masking is the improvement in function between the diotic versus monotic condition, or the antiphasic versus homophasic conditions. In other words, the ability of the ear to detect the desired signal in the presence of masking presented to both ears versus signal and noise in only one ear, or when the signal and noise are in or out of phase from each other. The ability for the ear to improve detection through the release from masking effect is thought to occur at the level of the brainstem, and thus, is potentially a good measure for ear disease, such as brainstem lesions or central nervous pathology below the auditory cortex, such as multiple sclerosis.

Considering the performance of understanding speech in the presence of noise, there are several deficits that may emanate from the auditory end organ or lower brainstem processes, and deficits that require higher-level cognitive skills to achieve average performance. The design of the MLDD test, in addition to the assessment of functional hearing, allows for more isolated measurement of end organ (cochlear distortion effects) and brainstem level function by measuring speech-in-noise in both monotic and diotic conditions. Additionally, the MLDD test reduces the cognitive load in the signal material by using digits, subsequently reducing the opportunity for comorbid variables introduced by context and learned speech. Thus, the MLDD test offers advantages over other speech-in-noise tests: a test sensitive to diseases that involve the end organ, auditory nerve, and brainstem through the measurement of binaural release from masking (a higher-order speech-in-noise task), as well as offering a test that is resistant to malingering, in that it limits an individual's ability to misreport clearly recognized items on the test. Thus, three goals of the MLDD test are to: 1) relate speech recognition in noise to functional hearing difficulties; 2) improve the ability of speech discrimination tests in the detection of ear disease involving the end organ and/or lower brainstem; and 3) control for volitional misrepresenting of functional disability.

To understand how the test works, one first must understand how common everyday sounds are localized and the importance of binaural processing. For example, when listening to music emanating from a single speaker in an otherwise quiet room, all of the instruments in the music recording appeared to emanate from a single location (the speaker). Perceptually, the easiest sound to listen to in this situation is the loudest sound. When listening to a stereo recording using two or more speakers located in different positions in an otherwise quiet room, the location of specific musical instruments in space can be perceived. When sound sources have different locations in space, it is much easier to focus on and clearly hear characteristics of the instrument, with less intrusion of the sound created by other instruments. In other words, hearing in stereo makes it easier to pay attention to sounds that are not necessarily the loudest sound.

One reason stereophonic recordings produce acoustic images in space is related directly to the nature of the sound striking each ear. Spatialized noise is a noise that has a certain origin in space. With changes in spatial location, the spectrum of the sound striking each ear changes systematically as a result of head shadow effects, pinna resonances, and subtle differences in the time of arrival of the sound to each ear (temporal structure). When the auditory system has sufficient fidelity, and specific brainstem pathways are intact, these acoustic cues converge to allow for the localization of the sound in space, and contribute to the emergence of the "release from masking effect." The release from masking effect refers to the inability of one sound to mask or otherwise cover perception of a second sound. When the sounds of music emanate from one speaker, the loudest sound tends to perceptually mask the less intense sounds. When sounds emanate from different spatial locations, as occurs with a stereophonic recording, the loudest sound does not necessarily mask other sounds in the music signal.

Most digits in noise tests present spoken digits in one ear, against a background of noise presented in the same ear. These tests do not measure the release from masking effect, are insensitive to certain brainstem lesions, and cannot be used for disability purposes because one cannot tell whether the person being tested is giving their best effort. The MLDD test measures the release from masking effect, making it more sensitive as a medical diagnostic test, and is designed to measure speech recognition in noise performance for functional or disability assessment purposes. By changing the spectral and temporal structure of masking sounds presented in both ears, one can manipulate the magnitude of the release from masking effect, and thereby vary test difficulty without changing the perceived loudness of the masking sound. As a result, it is possible to create 'catch' trials where listeners cannot determine when the masking noise has no effect on digit recognition, similar to a pure tone Stenger test used in everyday audiometric assessment (where the listener is presented with the same type of sound in both ears and is perceived as a single sound).

The MLDD test involves the use of digits (single numbers) and speech-weighted noise. Digits are over learned, redundant speech stimuli that can be recognized using low or high frequency speech energy. In other words, it is presumed that the use of digits would be less affected by various audiometric thresholds (e.g. low or high frequency hearing loss). This test is expected to be relatively immune to audibility and cortical factors and produces a relatively steep psychometric function, which can be estimated using limited presentation levels. For these reasons, the test is fast to administer in the clinical setting.

The MLDD test uses single digits (e.g., 1, 2, 3, 4, 5, 6, 7, 8 and 9), created using the IBM speech software. Test items are grouped into sets. In one example embodiment of the MLDD test, a set of four digits are presented to one ear with either noise in the same ear, or noise in both ears. The set of digits is followed by a five second response period. The participant's task involves listening to the four digits presented individually to the left and right ear, and then repeating the digits back (in order) during the response period. The digits are presented in the presence of background noise with varying signal-to-noise ratios. Signal-to-noise ratio (SNR) is the difference between the level of the signal and the level of the background noise. The MLDD test measures performance at four different SNRs providing moderate levels of masking. In some embodiments, a goal of the test is to determine the level at which the participant can correctly identify 50% of the digits.

In some embodiments, the methods provided herein can detect when measured speech recognition behavior does not reflect the listener's best effort. In some such embodiments, this is done by modifying the spectra or intra-aural temporal relationships in the presented masking noise to produce conditions that do or do not influence subsequent digit recognition, independent of the subjective loudness of the competing masking noise. In some situations, the presented masking noise will sound less loud but affect digit recognition substantially. In other situations, the presented masking noise will sound subjectively louder, but have little effect on digit recognition in noise. By manipulating these parameters, one can determine when an inaccurate response is the result of the physical capabilities of the auditory system, or the subjects' tendency to not respond accurately in the presence of louder noise. In effect, the MLDD test decouples the usual relationship where louder background sounds affect speech perception more than softer background sounds, with an intention to show when performance cannot be explained by known limitations in the auditory system.

In some embodiments, the MLDD test encompasses: (1) a retro cochlear test, (2) a speech in noise, and (3) a malingering test. All three of the tests can be covered by the performance of one MLDD test with a short administration time (e.g., less than 5 min in some embodiments). The MLDD test demonstrates promise in terms of disease detection and estimation of functional disability.

Referring to FIG. 1, an example MLDD test 100 can be performed to assess a participant's speech understanding in the presence of background noise. The depiction of MLDD test 100 pertains to the testing of a single ear of the participant. Generally, MLDD test 100 will be performed on both ears of the participant. That is, MLDD test 100 will be performed a first time for the participant's first ear, and then MLDD test 100 will be repeated a second time for the participant's second ear.

Example MLDD test 100 includes two major portions (test portions 110 and 160). The two portions 110 and 160 are the same except for the manner in which background noise is presented to the participant during the test 100.

The first test portion 110 is a series of tests performed while background noise is presented only to the ear being tested (this is also referred to herein as "monotic"). For example, if the participant's right ear is being tested, during first test portion 110 background noise is presented to the participant's right ear, but no background noise is presented to the participant's left ear. Similarly, if the participant's left ear is being tested, during first test portion 110 background noise is presented to the participant's left ear, but no background noise is presented to the participant's right ear.

The second test portion 160 is a series of tests performed while background noise is presented to both of the participant's ears (this is also referred to herein as "diotic"). For example, if the participant's right ear is being tested, during second test portion 160 background noise is presented to the participant's right ear, and background noise is presented to the participant's left ear. Similarly, if the participant's left ear is being tested, during second test portion 160 background noise is presented to the participant's right ear, and background noise is presented to the participant's left ear.

Each of the test portions 110 and 160 includes four sub-portions that have respectively differing SNRs (signal-to-noise ratios). For example, first test portion 110 (which presents background noise only in the ear being tested) includes: (i) a first sub-portion 120 during which the SNR is at a first level; (ii) a second sub-portion 130 during which the SNR is at a second level; (iii) a third sub-portion 140 during which the SNR is at a third level; and (iv) a fourth sub-portion 150 during which the SNR is at a fourth level. Similarly, the second test portion 160 (which presents background noise in both ears) includes: (i) a first sub-portion 170 during which the SNR is at a first level; (ii) a second sub-portion 180 during which the SNR is at a second level; (iii) a third sub-portion 190 during which the SNR is at a third level; and (iv) a fourth sub-portion 200 during which the SNR is at a fourth level.

The first, second, third, and fourth SNR levels differ from each other. For example, in some embodiments the first, second, third, and fourth SNR levels are about −2 dB, −6 dB, −10 dB, and −14 dB. In some embodiments, other SNR levels are used. For example, in some embodiments the first, second, third, and fourth SNR levels are about −3 dB, −6 dB, −9 dB, and −12 dB. It should be understood that any combination of differing SNR levels can be used for MLDD test 100. The sequence of performing the sub-portions 120, 130, 140, and 150 can be in any order.

In the depicted embodiment of MLDD test 100, within each of the sub-portions 120, 130, 140, 150, 170, 180, 190, and 200 individually, a series of four digits is audibly presented four times. For example, using sub-portion 120 as a representative example, while the SNR is at the first level and presented only in the ear being tested, a first group of four digits 122a is audibly presented, then a second group of four digits 122b is audibly presented, then a third group of four digits 122c is audibly presented, and then a fourth group of four digits 122d is audibly presented. By way of non-limiting example, the first group of four digits 122a may be "3, 8, 1, 5." The second group of four digits 122b may be "7, 5, 2, 9." The third group of four digits 122c may be "8, 1, 4, 6." The fourth group of four digits may be "6, 8, 3, 6." It should be understood that any grouping of single digits can be used.

After the presentation of each group of four digits 122a, 122b, 122c, and 122d, the participant is given time to respond by identifying, to the best of the participant's ability, the four digits that were audibly presented to the participant. For example, after the first group of four digits 122a has been audibly presented, then the participant gives a first response 124a that is an attempt to correctly identify the first group of four digits 122a. After the second group of four digits 122b has been audibly presented, then the participant gives a second response 124b that is an attempt to correctly identify the second group of four digits 122b. After the third group of four digits 122c has been audibly presented, then the participant gives a third response 124c that is an attempt to correctly identify the third group of four digits 122c. After the fourth group of four digits 122d has been audibly presented, then the participant gives a fourth response 124d that is an attempt to correctly identify the fourth group of four digits 122d. In sum, during sub-portion 120 the participant is audibly presented with 16 single-digit numbers (in four groups of four single-digit numbers).

The participant's responses 124a, 124b, 124c, and 124d can be made/registered in the form of written responses, oral responses, button-pushing responses (e.g., through a user interface), and by any other suitable form.

The participant can receive one or more scores pertaining to the participant's performance of sub-portion 120 (and of each of the other sub-portions individually). One type of score can be a percentage of the 16 single-digit numbers that the participant correctly determined during sub-portion 120. For example, if the participant correctly identified 12 of the 16 digits that were presented during the participant's performance of sub-portion 120, the participant can receive a score of 75% (12/16×100%) for sub-portion 120. Other types of statistical scoring can also be used.

Each of the other sub-portions 130, 140, 150, 170, 180, 190, and 200 can be performed in a manner analogous to the performance of sub-portion 120 as described above. That is, the performance of each other sub-portion 130, 140, 150, 170, 180, 190, and 200 can include the audible presentation of 16 single-digit numbers (in four groups of four single-digit numbers), and after each group of four single-digit numbers the participant can be given time to identify the digits that were audibly presented. Scores can be determined for each sub-portion 120, 130, 140, 150, 170, 180, 190, and 200 individually, of each test portion 110 and 160 individually, each level of SNR individually, and in any of a variety of other combinations.

As described above, second test portion 160 is a series of tests performed while background noise is presented to both of the participant's ears. In some embodiments, the background noise presented to both of the participant's ears is the same.

Alternatively, in some embodiments the background noise presented to the participant's ears is not the same in each ear. That is, in some embodiments the spectral and/or temporal structure of the background masking sounds presented is different in one of the participant's ears in respect to the other of the participant's ears. Using such variations, one can manipulate the magnitude of the release from masking effect, and thereby vary test difficulty without changing the perceived loudness of the masking sound. As a result, it is possible to create 'catch' trials where listeners cannot determine when the masking noise has no effect on digit recognition, similar to a pure tone Stenger test used in everyday audiometric assessment (where the listener is presented with the same type of sound in both ears and is perceived as a single sound). Accordingly, in some embodiments the MLDD test 100 can measure the release from masking effect, making it more sensitive as a medical diagnostic test, and capable of measuring speech recognition in noise performance for functional or disability assessment purposes.

To summarize, in some embodiments the MLDD test 100 is a test that combines a digits-in-noise paradigm and a release from masking paradigm to assess primitive speech (digit) recognition in spatialized noise. In particular embodiments, the MLDD test 100 assesses the release from masking effect by modifying the spectral and temporal structure of masking noise independent of the overall perception of loudness. In various embodiments of MLDD test 100, malingering performance can be detected, making the test useful for quantification of the functional (ICF) aspect of the deficit in speech in noise recognition. In addition, the participant's performance of MLDD test 100 can be used to indicate the presence of disease affecting the participant's auditory system.

In some embodiments, a third test portion is used that is somewhat analogous to test portions 110 and 160. The third test portion includes presenting the single-digit number in one ear while presenting background noise in the opposite ear.

While in some cases the MLDD test 100 can be performed using specialized audiology testing equipment, in other cases the MLDD test 100 can be conveniently performed using a personal computer (e.g., a desktop, a laptop, tablet, a smart phone, and the like). In other words, in some embodiments the MLDD test 100 can comprise computer-coded executable instructions that can be run on a computing device such as a personal computer. In some such embodiments, the participant can wear headphones that are connected with the personal computer, and the executable instructions of MLDD test 100 can be functioning on the personal computer. The participant can interact with the personal computer, for example, by inputting participant responses via the user interface of the personal computer. The MLDD test 100 functioning on the personal computer can automatically transition from one sub-portion to another, from one test portion to another, and from one ear to another. At the end of the MLDD test 100, the personal computer can calculate the participant's score and present various graphical and/or numerical results. In some cases, verbal descriptions pertaining to the participant's performance, and/or an analysis of the participant's hearing abilities, can also be presented by the personal computer.

EXAMPLES

A study was performed in which two groups of participants were tested using the audiology test methods described herein. A "young group" consisted of 53 normal hearing young adults; 18 males, 35 females (Mean age=23.4 years, range=18-33 years). All passed pure-tone hearing screen (octave frequencies 0.25-8 kHz) and SCAN-3 Screening Test (Keith, 2009). An "older group" consisted of 45 patients seen for routine hearing checks; 17 males, 28 females (Mean age=39.5 years; range=28-88 years). All had pure-tone thresholds at 0.5, 1, and 2 kHz≤25 dB HL.

Each participant of the two groups was subjected to the MLDD test procedure. Single-digit stimuli were presented at a fixed level of 48 dB HL. Speech-shaped background noise at 50, 54, 58, 62 dB HL was presented. The digit recognition threshold (50% detection level) SNRs were determined for the monotic (SmNm) and diotic (SmNo) presentation conditions (mSNR and dSNR respectively).

The study's objectives included: (i) establishment of normal values for SNRs in the diotic versus monotic conditions, and the calculated MLD, (ii) determination of list equivalency for four digit lists in young listeners with normal hearing, (iii) determination of ear effects for young listeners with normal hearing, and (iv) evaluation of age effects by comparing performance in young and older subjects with clinically normal hearing sensitivity.

The results were analyzed using linear regression modeling (e.g., R software) to evaluate list, ear and age effects on mSNR, dSNR and MLDD ($p<0.01$). The 50% detection level was estimated using a fitted normal distribution (least squares fit) for monotic (SmNm) and diotic (SmNo) conditions.

Figure 2:
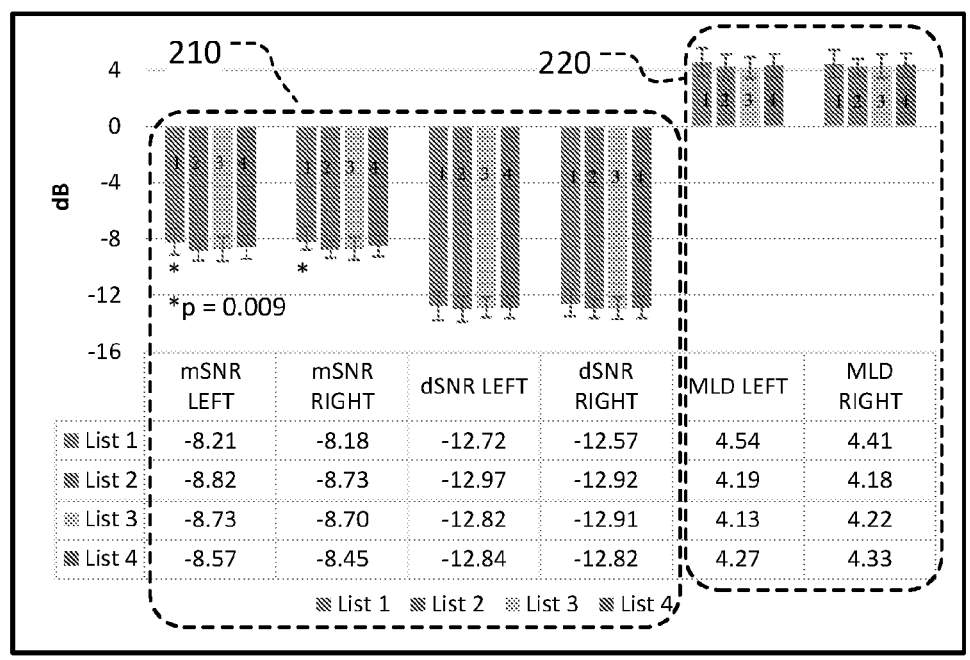
FIG. 2 is a graph showing a comparison of four sequences of digits and a comparison of the results of monotic noise versus diotic noise tests.

Referring to FIG. 2, tests were run to assess list equivalency and ear effects. The results of the tests are graphically displayed in a graph 200. Graph 200 includes: (a) the results of the list equivalency test in a first graphical region 210, and (b) the results of the ear effects test in a second graphical region 220.

Four different lists were compared: List 1, List 2, List 3, and List 4. Each of the lists was a sequence of 64 single-digit numbers (as described above in reference to MLDD test 100). List 1, List 2, List 3, and List 4 are each different sequences of 64 single-digit numbers. The list equivalency test results are shown in graph 200 within the first graphical region 210. The means and standard deviations of the SNR threshold value (i.e., the SNR level resulting in a 50% accuracy rate) are listed and charted. The comparative results show equivalency of the lists in each of four different contexts: (i) monotic background noise in the left ear with digits presented in the left ear, (ii) monotic background noise in the right ear with digits presented in the right ear, (iii) diotic background noise with digits presented in the left ear, and (iv) diotic background noise with digits presented in the right ear.

The results of the ear effects test are shown in the second graphical region 220. The values listed and charted are the differences in the SNR threshold values of monotic versus diotic background noise, on an individual ear basis. The data shows no ear effects. That is, the participant's test results were essentially the same in each ear.

Figure 3:
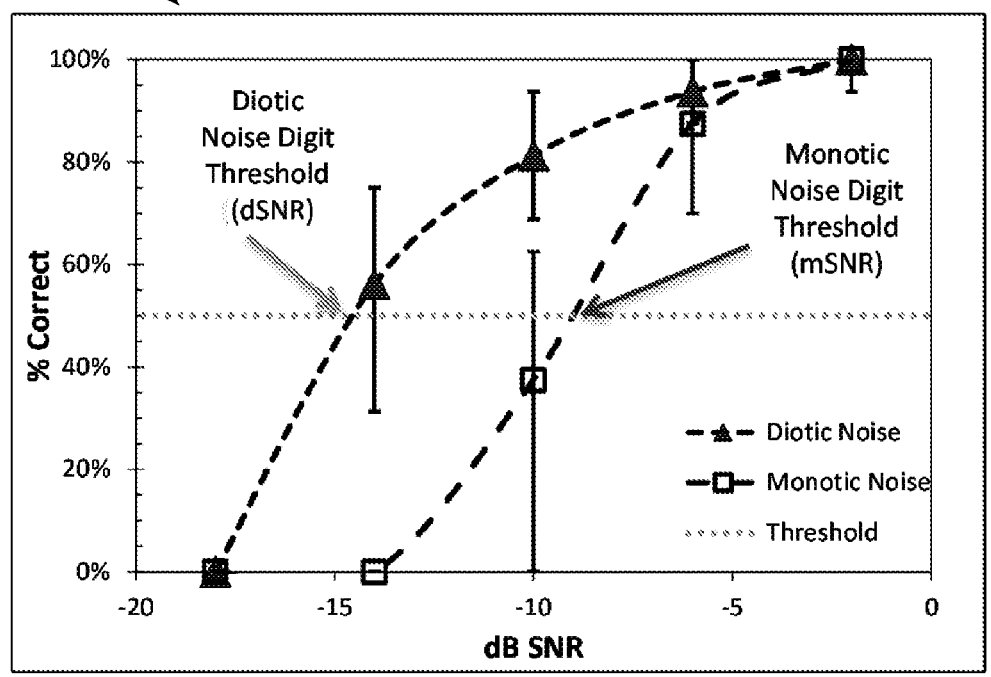
FIG. 3 is a graph showing monotic noise and diotic noise test results at four different signal to noise ratios.

Referring to FIG. 3, a graph 300 shows the participant's results (i.e., % correct) at each SNR (−2 dB, −6 dB, −10 dB, and −14 dB) for diotic background noise and monotic background noise. This shows that participants performed better on the diotic background noise test in comparison to the monotic background noise test, as a function of SNR. For example, graph 300 shows that the average correct at a SNR of −10 dB was about 80% in the diotic test and about 35% in the monotic test. This graph 300 shows data curves that may allow the MLDD tests described herein to be performed using fewer SNR levels, while still yielded accurate results.

Figure 4:
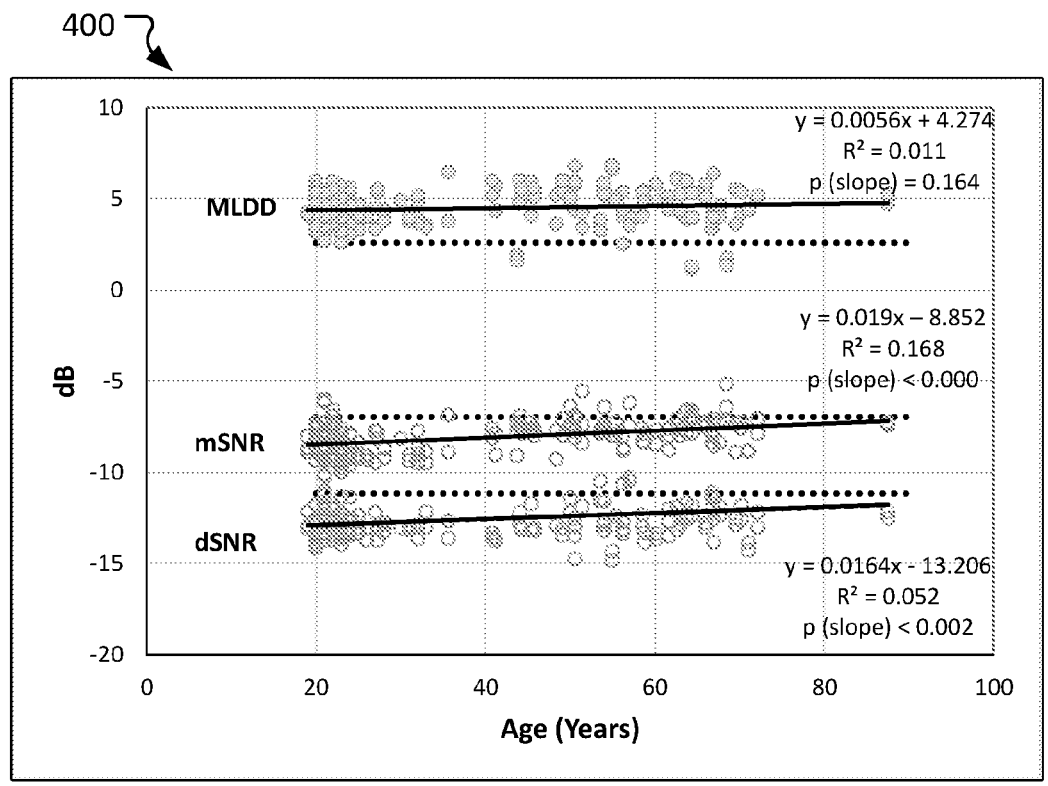
FIG. 4 is a graph showing the effects of age on monotic noise and diotic noise test results.
Figure 5:
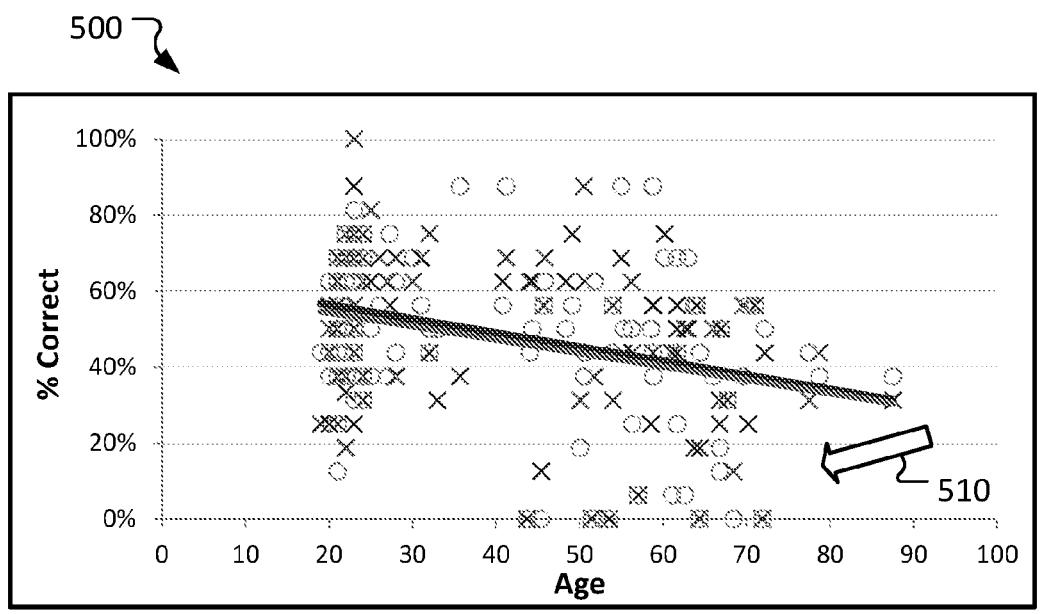
FIG. 5 is a graph showing the effects of age on diotic noise test scores.

Referring to FIGS. 4 and 5, graphs 400 and 500 shows age effects. These graphs 400 and 500 show the MLDD test results of participants with "normal hearing" across an age range.

Graph 400 plots age effects on mSNR, dSNR, and MLDD in young (one randomly selected list per ear) and old adults combined. No ear effect was found in any regression (all p>0.06). Regression line slopes for mSNR and dSNR were significant (p<0.01). The dotted line on each graph is the 97.5% limit for the young group, assuming no age effect. In the older group, 11%, 12% and 8% of scores were below expected limits in the mSNR, dSNR and MLDD distributions respectively (expected frequency≤2.5%). Low MLDD scores were the result of poor dSNR scores 86% of the time (6/7 cases). However, 59% (7/17) of cases with low mSNR or dSNR scores did not result in a correspondingly low MLDD.

Graph 500 plots age by Diotic Score and Ear at −14 dB SNR (X=Left Ear, O=Right Ear; solid lines=liner regression trend lines). Age effect on individual scores for both ears in the diotic condition at −14 dB SNR are shown. While the majority of scores in the old group fell in the range of scores expected based on younger group performance, the regression line was pulled down by the performance of a subgroup of older subjects test scores (arrow 510). So older group performance was heterogeneous.

In summary, graphs 400 and 500 show that most of the participants did well on the MLDD test, across the age range, but that there are some participants that fail substantially, and it is not a function of noise. It can be seen that there is a statistically significant age effect, and that within the older participant group there are two sub-groups (i.e., one sub-group that retains the stability and another sub-group that fails). Graphs 400 and 500 shows that the MLDD tests provided herein can identify participants that have a speech-in-noise problem that is not related to conventional hearing loss.

Of the four MLDD lists, list 1 was slightly harder than the remaining lists in the monotic condition (~0.5 dB lower mSNR score; see FIG. 2). Although statistically significant, the observed difference was small, and of questionable relevance given the spread of scores across subjects and conditions.

No ear effect was measured in any condition (see FIG. 2). Specifically, a right ear dominance was not observed, likely because of the low linguistic load of digits as stimuli. It does not appear that language driven cerebral dominance effects are a cofactor in the assessment of supra-threshold auditory resolution or release from masking effects on the MLDD.

Age effects were evident in group data (see FIG. 4). Specifically, mSNR and dSNR scores trended lower with age. The release from masking effect was relatively impervious to age. However, when a reduction in the MLDD was observed, it was driven by poor performance on the SmNo condition (dSNR score; see FIG. 5). In contrast, in over half of cases where poor performance was observed in SmNm and or SmNo conditions, the release from masking effect was preserved. This may imply that poor performance on the MLDD test can be stratified into age related effects, release from masking effects, and other, general auditory channel factors. All would be relatively independent of pure tone hearing sensitivity or higher order linguistic processes. Hence, the MLDD tests provided herein may play a useful role in understanding the underpinnings of impaired speech recognition in noise.

Finally, digits in noise-based protocols are being developed to detect hearing problems as telephone based hearing screening applications. We show a clear age effect for this type of task. But, based on our preliminary data, the false positive rate would be on the order of 11-12% (see FIG. 4) across ages up to 80 years.

The MLDD tests provided herein measure auditory channel capability relatively independent of linguistic processing. Comparing performance on this test with more linguistically dependent measures may help further understand the problem of speech recognition in noise.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A hearing test system for testing a participant's ability to accurately detect speech in a presence of background noise, the system configured to:
   audibly present a first series of single-digit numbers to a first ear of the participant while a first background noise at a first signal-to-noise ratio (SNR) is audibly presented to the first ear but not to a second ear of the participant;
   receive, from the participant, a first group of results that reflect a participant's attempt at accurately reproducing the first series of single-digit numbers;
   audibly present a second series of single-digit numbers to the first ear while a second background noise at a second SNR is audibly presented to the first ear and to the second ear;
   receive, from the participant, a second group of results that reflect the participant's attempt at accurately reproducing the second series of single-digit numbers;
   audibly present a third series of single-digit numbers to the second ear while a third background noise at a third SNR is audibly presented to the second ear but not to the first ear;
   receive, from the participant, a third group of results that reflect the participant's attempt at accurately reproducing the third series of single-digit numbers;
   audibly present a fourth series of single-digit numbers to the second ear while a fourth background noise at a fourth SNR is audibly presented to the second ear and to the first ear; and
   receive, from the participant, a fourth group of results that reflect the participant's attempt at accurately reproducing the fourth series of single-digit numbers.

2. The system of claim 1, wherein the system comprises a personal computer.

3. A method of testing a participant's ability to accurately detect speech in a presence of background noise, the method comprising:
   audibly presenting a first series of single-digit numbers to a first ear of the participant while a first background noise at a first signal-to-noise ratio (SNR) is audibly presented to the first ear but not to a second ear of the participant;
   receiving, from the participant, a first group of results that reflect a participant's attempt at accurately reproducing the first series of single-digit numbers;
   audibly presenting a second series of single-digit numbers to the first ear while a second background noise at a second SNR is audibly presented to the first ear and to the second ear;
   receiving, from the participant, a second group of results that reflect the participant's attempt at accurately reproducing the second series of single-digit numbers;
   audibly presenting a third series of single-digit numbers to the second ear while a third background noise at a third SNR is audibly presented to the second ear but not to the first ear;
   receiving, from the participant, a third group of results that reflect the participant's attempt at accurately reproducing the third series of single-digit numbers;
   audibly presenting a fourth series of single-digit numbers to the second ear while a fourth background noise at a fourth SNR is audibly presented to the second ear and to the first ear; and
   receiving, from the participant, a fourth group of results that reflect the participant's attempt at accurately reproducing the fourth series of single-digit numbers.

4. A method of testing a participant's ability to accurately detect speech in a presence of background noise, the method comprising:
   audibly presenting a first series of single-digit numbers to a first ear of the participant while a first background noise at a first signal-to-noise ratio (SNR) is audibly presented to the first ear but not to a second ear of the participant;
   receiving, from the participant, a first group of results that reflect a participant's attempt at accurately reproducing the first series of single-digit numbers;
   audibly presenting a second series of single-digit numbers to the first ear while a first type of second background noise at a second SNR is audibly presented to the first ear and while a second type of second background noise that differs from the first type of second background noise is audibly presented to the second ear;
   receiving, from the participant, a second group of results that reflect the participant's attempt at accurately reproducing the second series of single-digit numbers;
   audibly presenting a third series of single-digit numbers to the second ear while a third background noise at a third SNR is audibly presented to the second ear but not to the first ear;
   receiving, from the participant, a third group of results that reflect the participant's attempt at accurately reproducing the third series of single-digit numbers;
   audibly presenting a fourth series of single-digit numbers to the first ear while a first type of fourth background noise at a fourth SNR is audibly presented to the first ear and while a second type of fourth background noise that differs from the first type of fourth background noise is audibly presented to the second ear; and
   receiving, from the participant, a fourth group of results that reflect the participant's attempt at accurately reproducing the fourth series of single-digit numbers.

* * * * *